United States Patent [19]

Miller, Jr.

[11] Patent Number: 4,471,772

[45] Date of Patent: Sep. 18, 1984

[54] METHOD AND UNDERGARMENTS FOR PREVENTING PENILE TISSUE DETERIORATION

[76] Inventor: Taylor C. Miller, Jr., 210 Professional Ctr., Montgomery, Ala. 36104

[21] Appl. No.: 410,482

[22] Filed: Aug. 23, 1982

[51] Int. Cl.³ .............................................. A41B 9/12
[52] U.S. Cl. ........................................ 128/159; 2/403
[58] Field of Search .......................... 128/79, 158–162; 2/403–404

[56] References Cited

U.S. PATENT DOCUMENTS

| | | | |
|---|---|---|---|
| 3,229,692 | 1/1966 | Creed | 128/158 |
| 3,782,375 | 1/1974 | Donars | 128/158 |
| 4,206,752 | 6/1980 | Witton | 128/79 |
| 4,377,008 | 3/1983 | Jung | 128/159 X |
| 4,378,010 | 3/1983 | McDonald | 128/168 |

FOREIGN PATENT DOCUMENTS 25173  8/1908  Sweden .............................. 128/158

Primary Examiner—Dalton L. Truluck
Attorney, Agent, or Firm—Kenneth E. Darnell

[57] ABSTRACT

A method and articles of underwear for effecting the method, the invention intends the prevention of damage to erectile and other tissue of the penis, primarily to prevent or to alleviate impotence caused by penile circulatory deficiencies. The present method provides for support of the penis in attitudes within which the major vascular conduits of the penis are not subject to bending or crimping, a particular supportive mode being the maintenance of the flaccid penis in an upwardly directed attitude such that the longitudinal axis of the penis is maintained in an essentially straight line or at least in a gentle arc. The underwear configured according to the invention act to maintain the penis in the attitude intended by a practice of the present method and can further be configured to increase or decrease fertility to the degree affected by thermal considerations.

2 Claims, 11 Drawing Figures

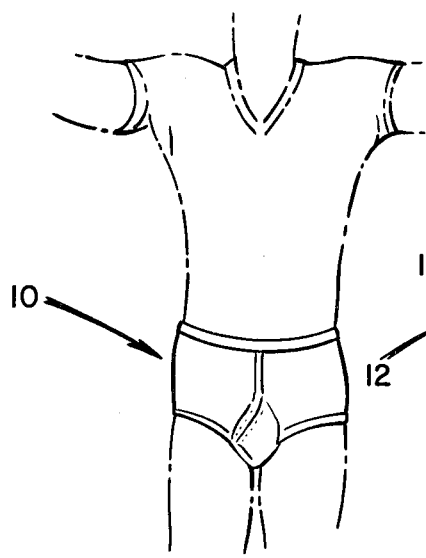
FIG. 1 PRIOR ART
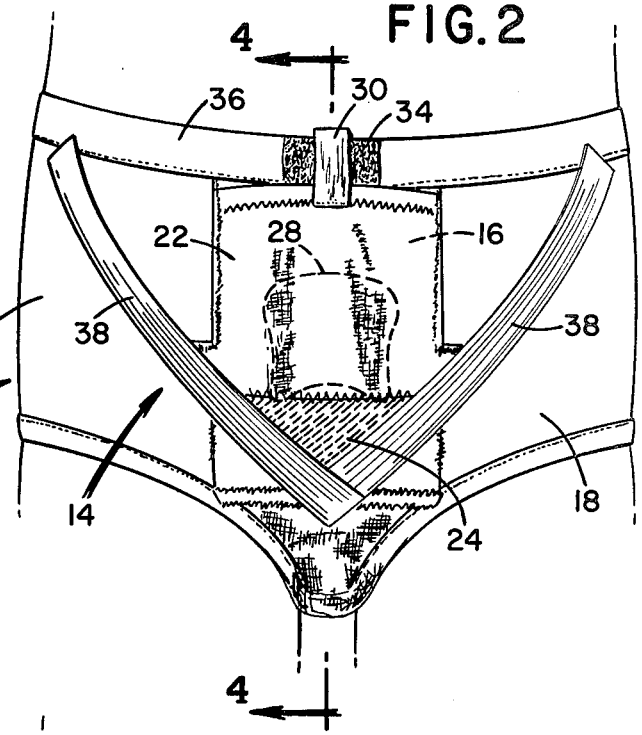
FIG. 2
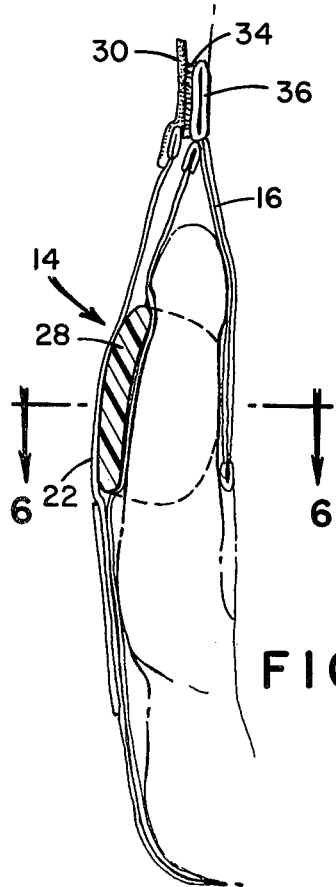
FIG. 4
FIG. 3
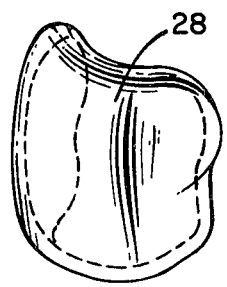
FIG. 5
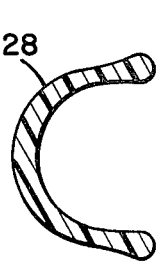
FIG. 6

METHOD AND UNDERGARMENTS FOR PREVENTING PENILE TISSUE DETERIORATION

BACKGROUND OF THE INVENTION

1. Field of the Invention

The invention relates generally to methods for maintaining sexual potency in males and particularly to a method and articles of underwear intended to prevent damage to erectile and other tissues of the penis.

2. Description of the Prior Art

Male sexual impotence is typically defined as the repeated inability to maintain an erection adequate to normal sexual function. While impotence has long been considered to be largely a psychological problem, it is now being recognized that physical causes may account for the great majority of such problems. A particular physical cause which has only recently been generally recognized is poor circulation of blood to the penis. In order to relieve such situations whereby blood deficiency within the penis causes impotence, a revascularization or "bypass" operation has been developed with considerable success. Such surgery involves the transplantation of a healthy artery from the abdomen to the penis wherein blood is then rerouted around the diseased artery to improve circulation. While this surgery is proving helpful in a majority of cases to counter an existing condition, neither this surgery nor other efforts have intended the prevention of circulatory problems in the penis and particularly circulatory problems which are caused by a simple though universal abuse of the penis. In particular, the penis is contorted out of shape and held within unnaturally confined quarters even from birth, this abuse being further exacerbated throughout life by the confinement of the penis within clothing such as "jockey shorts" which crumple the penis into the testes and maintain the penis in a substantially bent or crimped conformation. In order to appreciate the damage inflicted upon the penis by conventional undergarments, it should be understood that the erectile tissue of the penis essentially has two parts, each part being referred to generally as the corpus cavernosum and each containing an artery and a vein down its center to furnish blood for erection. The present invention recognizes that bending of the penis over a long period of time finally causes the corpus cavernosum to develop a kink which can be considered analogous to a kink in a length of hose. When the blood conduits are bent for sufficient period of time, such a kink develops and the kink becomes a perfect place for development of fatty deposits which result in a restriction of blood supply which becomes insufficient for proper function of erectile tissue. Even during athletics, when blood flow is increased, the penis is held within an athletic supporter with a resulting bending and kinking of the penis. Such undergarments further pull the testes tightly against the body and cause undesirable heating of the testes in addition to the restriction of blood flow in the general area.

Accordingly, the present invention provides a method and articles of underwear capable of maintaining proper circulation in the penis such that the vascular system of the penis will remain intact and will allow proper function of the erectile tissue and other tissues of the penis.

SUMMARY OF THE INVENTION

The invention provides a method and articles of underwear suitable for practicing the method, the primary intent of the invention being the prevention of damage to erectile and other tissue of the penis, thereby to prevent or to alleviate impotence caused by circulatory deficiencies in the vascular system of the penis. In order the support the penis in an unbent configuration and to allow natural cooling or warming of the testes, the present articles of underwear include structure capable of maintaining the penis in an upright attitude with at least medial portions of the penis being held and supported to maintain the penis in an uncrimped position so that interference of blood flow in the vascular system of the penis does not occur. The present articles of underwear are substantially to the "boxer" or "jockey" shorts conventionally worn with the exception that the forward scrotal portion of such underwear would be fully cut so as to allow the testes to naturally hang from the body of a wearer such that the testicles will be naturally pulled up against the body when cold and will naturally hang loosely from the body when warm. In this manner, the body maintains a desired temperature within the testes such that sperm is not destroyed by heat build up.

The penis itself is held in an unbent configuration by a sheath of soft material such as the materials from which underwear is typically formed, the sheath being held to form by a substantially rigid insert disposed within the sheath, the insert being dimensioned to fit at least partially about at least medial portions of the penis with the material forming the sheath actually contacting the penis. The sheath itself preferably extends upwardly and is maintained in position by fastening of upper portions of the sheath to the waistband of the underwear. The penis is thus held in an upright attitude such that the longitudinal axis of the penis is held in a straight line or in a slightly curved conformation to prevent crimping of the major vessels of the penile vascular system.

Underwear according to the invention suitable for athletic activity is further provided by means of the disposition of an elongated shield element held within a supporting pocket on an athletic supporter. The testes and penis are disposed within the shield with a pocket being formed to maintain the penis in an upright attitude. Accordingly, during periods of particularly high blood flow and heat loading, blood flow is not restricted within the penis due to the maintenance of the penis in an unbent configuration. Further, the testes are allowed to naturally hang from the body within the shield to allow necessary cooling. The shield itself is preferably provided with apertures which allow air circulation to facilitate cooling of the testes. In those situations where it is desired to allow heat loads to destroy sperm within the testes, the shield can be formed without apertures or can be provided with a plastic cover over the shield to prevent air flow through apertures in the shield. Thus, a degree of control can be exerted over fertility through wearing of the present undergarments.

Accordingly, it is the primary object of the present invention to provide a method and articles of underwear for preventing damage to erectile and other tissue of the penis.

It is another object of the present invention to provide a method and articles of underwear wherein the penis is maintained in an upright attitude to prevent bending and crimping of the major vessels of the penile vasculature, thereby to prevent or to alleviate impotence caused by penile circulatory deficiencies.

It is a further object of the invention to provide a method and articles of underwear for preventing damage to erectile and other tissue of the penis and to simultaneously exert control over fertility by providing for particular degrees of cooling or heating of the testes.

Further objects and advantages of the present invention will become more readily apparent in light of the following detailed description of the preferred embodiments.

BRIEF DESCRIPTION OF THE DRAWINGS

FIG. 1 is a perspective view illustrating conventional underwear according to the prior art;

FIG. 2 is a front elevational view of underwear configured according to the invention and suitable for normal wear;

FIG. 3 is an elevational view of the underwear of FIG. 2 with the penile contacting flap member shown in the unattached conformation;

FIG. 4 is a section taken along line 4—4 of FIG. 2;

FIG. 5 is a perspective view of a particular structural element utilized to support the penis;

FIG. 6 is a section of the structural element of FIG. 5;

DESCRIPTION OF THE PREFERRED EMBODIMENTS

Figure 7:
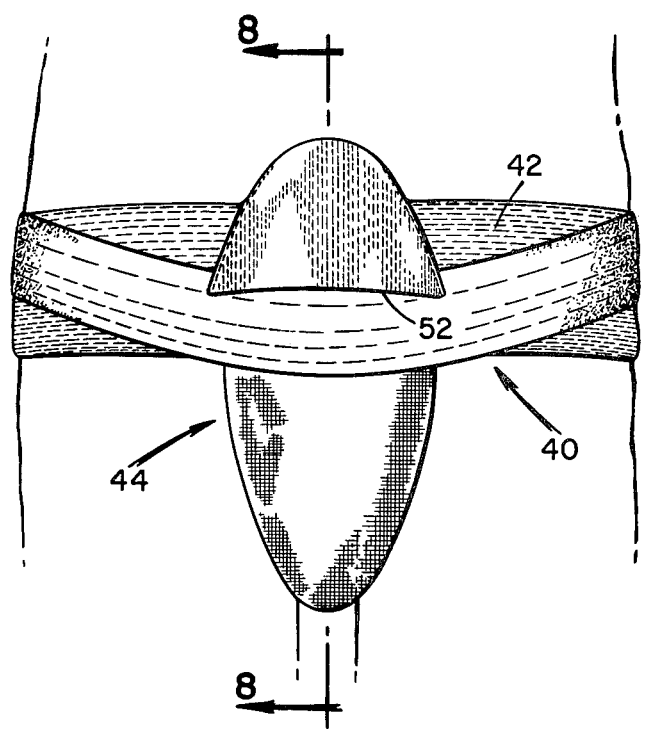
FIG. 7 is an elevational view of an athletic supporter configured according to the invention.

Referring now to the drawings and particularly to FIG. 1, conventional underwear is seen at 10 and is of the type over which the present invention intends improvement. In particular, the underwear 10 is seen to hold the penis and testes in a position substantially against the body with the penis typically being bent or held to the side in a manner which can cause crimping of the major vessels of the penile vasculature. Over time, this crimping can lead to blood flow deficiencies with in the penis and eventually result in the failure of erectile tissue to adequately function.

A first embodiment of the invention is seen in FIGS. 2-6 to comprise a pair of undershorts 12, the primary portions of which are substantially identical to that of conventional underwear. In particular, the portions of the undershorts 12 which fit about the waist, the hips, the buttocks and the legs are substantially identical to corresponding portions of the conventional underwear 10. However, the frontal portion of the undershorts 12, that is, the portion generally designated by the numeral 14, is seen to differ significantly from the corresponding portion of the conventional underwear 10. In particular, a front panel 16 is provided between the usual side panels 18, a pocket 22 joined to a reinforcement panel 24 adjacent the lower edge of the front panel 16. An opening 26 is thus formed between the lower edge of the front panel 16 and lower portions of the pocket 22.

The pocket 22 is seen to receive supporting sleeve 28, the fabric from which the pocket 22 is formed acting to contour itself about the arcuate surfaces of the sleeve 28 to effectively cause the sleeve 28 to be "lined" with the soft fabric material from which the pocket 22 is formed. An attachment flap 30 is seen to have a layer of a hook and eye fastening material formed on the inner side thereof as seen at 32, the layer 32 attaching to a corresponding patch 34 of similar material which is disposed on waistband 36 of the undershorts 12.

In use and as best seen in FIG. 4, median portions of the penis are received within the substantially semicircular confines of the supporting sleeve 28 with the sleeve 28 being disposed within the pocket 22 as aforesaid. With the penis thus medially supported, the pocket 22 is folded upwardly and maintained in an upwardly disposed attitude by attachment of the flap 30 to the patch 34 on the waistband 36 of the undershorts 12. As particularly seen in FIGS. 2 and 4, the penis is thus disposed in an upward attitude such that the longitudinal axis of the penis is substantially maintained in an unbent or uncrimped configuration. The major vessels of the penile circulatory system are thereby prevented from developing kinks which can cause circulatory deficiencies and lead to impotence due to failure of the circulatory system to adequately supply erectile tissues with blood.

It is to be understood that the supporting sleeve 28 can be otherwise configured and could actually take the form of complete rings or other supporting elements. The primary consideration is that the supporting element corresponding to the sleeve 28 be capable of maintaining a desired contact with the penis so as to support the penis in a desired orientation and reduce or eliminate the degree of bending to which the penis is subjected. The size of the pocket 22 is preferably dimensioned such that the sleeve 28 fits in a virtual form-fitting manner when the pocket is pulled into a conforming relation with the supporting sleeve 28. Elongated reinforcement strips 38 may also be provided on the undershorts 12 in order to maintain the pocket 22 in a desired position. It is also to be understood that the supporting sleeve 28 can be formed of a rigid material such as any of the "plastics" or can be formed of a substantially rigid material such as hard rubber or the like. As will also be noted in FIG. 4, the undershorts 12 are preferably cut in a full manner in the area below the reinforcement panel 24 in order that the testes are not unnaturally pulled against the body.

Figure 8:
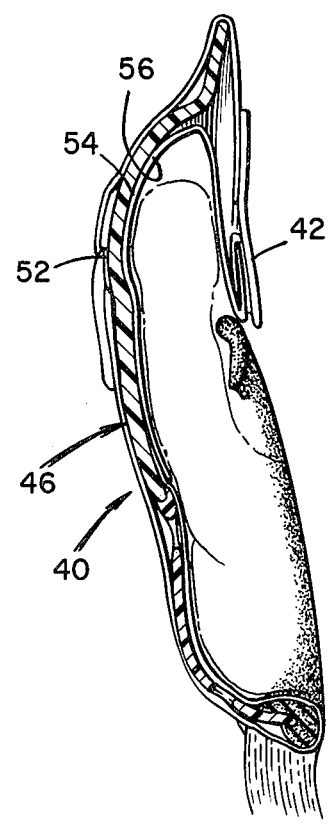
FIG. 8 is a section taken along lines 8—8 of FIG. 7.
Figure 9:
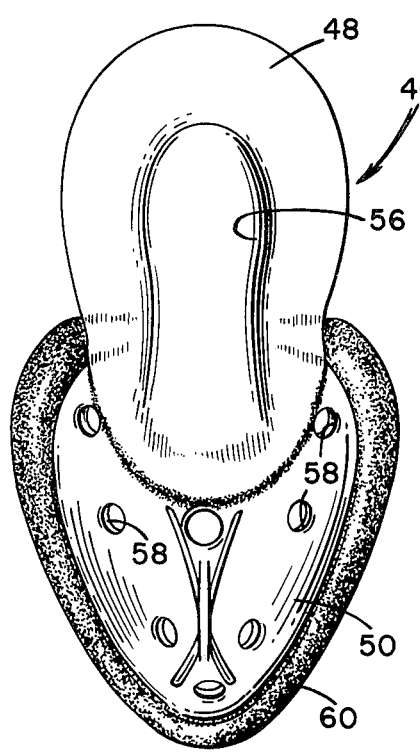
FIG. 9 is a front elevational view of a shield element used in the athletic supporter of FIG. 7.

Referring now to FIGS. 7-11, a further embodiment of the invention is seen to comprise an athletic supporter 40 conventionally comprised of a waistband 42 having a vertically elongated pocket 44 formed frontally of the supporter 40. The pocket 44 is seen to contain a shield 46, the structure of which is particularly seen in FIGS. 9-11. The shield 46 is seen to be comprised of an upper penis-mounting cup 48 and a lower testes shielding cup 50. The pocket 44 is best seen in FIG. 8 to encase the shield 46, the shield 46 being slipped into the pocket 44 through a slit-like opening 52 formed on the outward side of the pocket 44. As also as best seen in FIG. 8, an inner pocket 54 formed of a soft fabric-like material joins to a surface portion of a pocket 44 at one end of said inner pocket 54 and to the waistband 42 at the other end of the pocket 54. The inner pocket 54 can effectively be formed of a substantially rectangular flap of material which can be formed into a pocket-like pouch which receives the penis and which holds the penis in an upright attitude by virtue of the fitting of the inner pocket 54 into a vertical depression 56 formed in the inward surface of the cup 48. The depression 56 is seen to be dimensioned to receive the penis held within the inner pocket 54.

The testes-shielding cup 50 can take the general form of the usual cup which is provided with an athletic supporter as used in certain conventional athletic endeavors. The cup 50 can be provided with apertures 58 which allow passage of air in contact with the testes to prevent overheating of the testes. Further, a soft plastic border 60 can be provided about the periphery of the cup 50 to increase comfort to a wearer.

Figure 11:
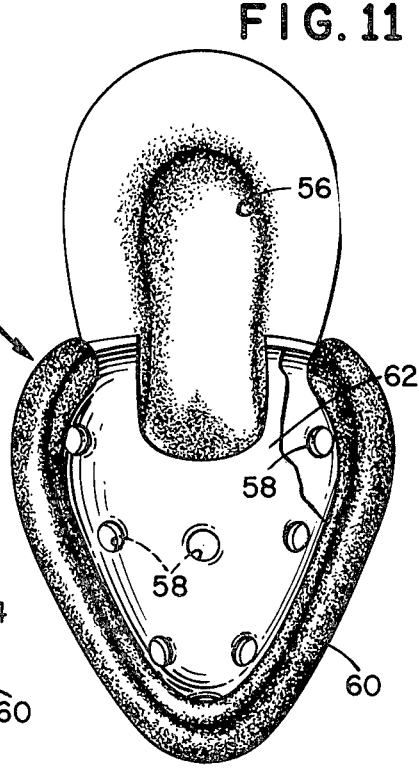
FIG. 11 is a rear elevational view of the shield element.

As seen particularly in FIG. 11, a cover 62 can be provided over the cup 50 to close off the apertures 58, thereby to prevent cooling air flow and to increase the heat loading experienced by the testes. Alternately, the cup 50 could be formed without the apertures 58 to produce the same result, that is, the intentional increase in heat loading so as to facilitate sterilization of sperm within the testes and thus act as a supplemental birth control measure as desired. Use of the cover 62 has the advantage of allowing the user to utilize the same shield 46 for either allowing air flow or reducing air flow as desired.

Figure 10:
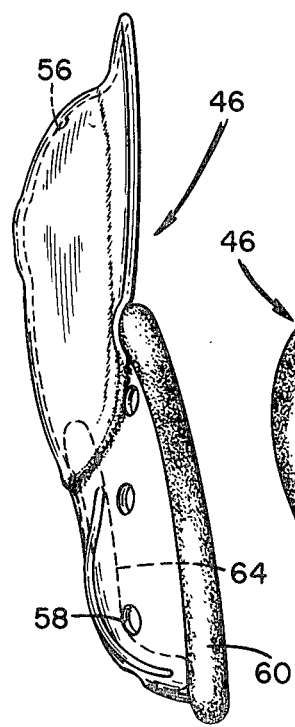
FIG. 10 is a side elevational view of the shield element.

Referring now to FIG. 10, a pad 64 can be seen to be placed within the interior of the shield 46, the pad being moistened with water or similar evaporable liquid so that cooling additional to air flow can be experienced by the testes. In such a situation, the cooling facilitates fertility by providing additional assurance that heat loading does not kill sperm within the testes.

It is to be understood that the present method can be practiced other than as explicitly described above and that the articles of underwear thus described can be otherwise configured than as explicitly described without departing from the intended scope of the invention. Accordingly, the scope of the invention is to be defined in light of the foregoing description and in particular accordance with the appended claims.

What is claimed is:

1. In an article of underwear formed of a fabric and adapted to be worn by a male about the hips, the improvement comprising:

a fabric pocket attached to a front portion of the underwear;

a supporting element disposed within the pocket for engaging and supporting the penis to hold the penis in an unbent, upwardly directed attitude;

a cup element attached to a lower portion of the supporting element and being disposed in the pocket, the cup element being disposed over and acting to shield the testes, the cup element having apertures formed therein to provide cooling air flow to the testes; and means for selectively covering the apertures in the cup element to block air flow to the testes, said means comprising a cover removably affixed to the cup element.

2. In the article of claim 1 wherein the improvement further comprises a pad element disposed in the cup element and moistened with an evaporable liquid to facilitate cooling of the testes.

* * * * *